United States Patent [19]

Crochemore

[11] Patent Number: 5,003,091
[45] Date of Patent: Mar. 26, 1991

[54] PREPARATION OF 3-MEMORY-4,5-METHYLENEDIOXYBEN-ZALDEHYDE

[75] Inventor: Michel Crochemore, Chaponost, France

[73] Assignee: Rhone-Poulenc Chimie, Courbevoie, France

[21] Appl. No.: 419,659

[22] Filed: Jan. 28, 1988

[30] Foreign Application Priority Data

Jan. 28, 1987 [FR] France ............... 87 01175

[51] Int. Cl.$^5$ .......................................... C07D 317/64
[52] U.S. Cl. ................................................. 549/436
[58] Field of Search ........................................ 549/436

[56] References Cited

U.S. PATENT DOCUMENTS

| | | | |
|---|---|---|---|
| 3,840,605 | 10/1974 | Gordon | 568/671 |
| 3,992,432 | 11/1976 | Napier et al. | 568/489 |
| 4,427,666 | 1/1984 | Munes et al. | 549/436 |

FOREIGN PATENT DOCUMENTS 2130656 3/1972 France .

OTHER PUBLICATIONS

Freeman et al., Tetrahedron Letters, No. 38, pp. 3251–3254 (1975).
Fujita et al., Chemical Abstracts., vol. 85, No. 46191w, "Aromatic Alkylenedioxy Compounds".
Iinuma et al., Yakugaku Zasshi, vol. 103, No. 9 (1983), "Synthesis of New Flavones of *Bauhinia Championii* in Formosa".

*Primary Examiner*—Nicky Chan
*Attorney, Agent, or Firm*—Burns, Doane, Swecker & Mathis

[57] ABSTRACT

3-Methoxy-4,5-methylenedioxybenzaldehyde is facilely and improvedly prepared by reacting 4,5-dihydroxy-3-methoxybenzaldehyde with a dihalomethane in a two-phase reaction medium and at a pH of from 7 to 12.

10 Claims, No Drawings

PREPARATION OF 3-METHOXY-4,5-METHYLENE-DIOXYBENZALDEHYDE

BACKGROUND OF THE INVENTION

1. Field of the Invention

The present invention relates to a simplified and improved process for the preparation of 3-methoxy-4,5-methylenedioxybenzaldehyde and, more especially, to such simplified/improved process employing a 4,5-dihydroxy-3methoxybenzaldehyde (or hydroxyvanillin) starting material.

2. Description of the Prior Art

3-Methoxy-4,5-methylenedioxybenzaldehyde is known to this art as a very important compound which is a useful intermediate for the synthesis of many alkaloids, pharmaceutical precursors and pharmaceuticals, per se.

Various techniques for the synthesis of 3-methoxy-4,5-methylenedioxybenzaldehyde have been proposed to the art.

Among the most recent, the following methods of preparation are representative:

An article in the *Bulletin of Chemical Society Japan* (Matsumoto, 1985, 58 (1), pages 346 to 351) describes a process which firstly consists in preparing methyl 4,5-methylenedioxy-3-methoxybenzoate by reacting dibromomethane with methyl 4,5-dihydroxy-3-methoxybenzoate and then in reducing the ester group into a CH$_2$OH group with lithium aluminum hydride and, finally, in oxidizing this primary alcohol group thus created into an aldehyde group. According to the article, the overall yield of this three-stage synthesis is 57%. This process is far too complicated and the productivity thereof is too low for it to be employed industrially.

In an article in *Chemische Zeitung* (Dallacker 1984, 108, (5) pages 186–187), another preparative method is described. It consists in starting with 4,5-methylenedioxy-3-methoxyaniline in order to form 5-bromo-1,2-methylenedioxy-3-methoxybenzene; the bromine is then replaced by an aldehyde group. The overall yield of this synthesis is approximately 37%. Like the above process, this process is complicated and the productivity thereof is too low for it to be employed on an industrial scale.

Another article in *Journal of Chemical Society Perkin Trans.* (1, 1984 (4) pages 709–712 by McKiftrick and R. Stevenson) describes a procedure which forms a methylenedioxy bridge on hydroxyvanillin. The reaction between hydroxyvanillin and dibromomethane in the presence of potassium carbonate is carried out in dimethyl sulfoxide. As the recovery of the final product requires a treatment with water, this makes the recycling of the very expensive solvent difficult. No yield is specified.

The processes of the prior art typically entail the formation of the aldehyde group in the final stage; the process mentioned immediately above, which consists in forming a methylenedioxy bridge on a compound already bearing an aldehyde substituent, employs a solvent which is expensive and difficult to recycle.

SUMMARY OF THE INVENTION

Accordingly, a major object of the present invention is the provision of an improved process for the synthesis of 3-methoxy-4,5-methylenedioxybenzaldehyde, which is simple and which can readily be carried out on an industrial scale.

Briefly, the present invention features the preparation of 3-methoxy-4,5-methylenedioxybenzaldehyde by reacting 4,5-dihydroxy-3-methoxybenzaldehyde and dihalomethane, and wherein the reaction is carried out (a) in a two-phase medium of water and a liquid organic compound, and (b) at a pH of from 7 to 12.

DETAILED DESCRIPTION OF THE PREFERRED EMBODIMENTS OF THE INVENTION

More particularly according to the present invention, it will be appreciated that 4,5-dihydroxy-3-methoxybenzaldehyde is a compound which can readily be prepared, notably from vanillin, a common industrial material.

The halogenation, especially bromination, selective for vanillin, in the ortho position relative to the hydroxyl group, is carried out industrially. The hydrolysis of the halovanillin thus formed is also an industrial reaction for the production of 4,5-dihydroxy-3-methoxybenzaldehyde (or hydroxyvanillin).

The dihalomethane which serves as both the reagent and the organic phase in the process is more particularly selected from among symmetrical or mixed chlorinated and brominated derivatives. Thus, dichloromethane, dibromomethane, chlorobromomethane, or mixtures thereof, are advantageously employed.

In practice, dichloromethane, which is the most common and the least expensive compound, will preferably be used.

The pH of the medium is maintained at a value of from 7 to 12 throughout the reaction period. Therefore, the hydrogen halide which is formed must be neutralized. An aqueous alkaline solution may, for example, be added continuously. In general, an aqueous solution of an alkali metal hydroxide or carbonate, most typically an aqueous solution of sodium hydroxide, will be employed.

In order to achieve an adequate reaction rate, while preventing any side reactions to the greatest possible extent, the reaction is preferably carried out at a pH of from 8 to 10.

Although the use of dihalomethane as the organic phase in the process according to the invention is preferred, its role as the bridging agent between the two hydroxyl groups of 4,5-dihydroxy-3-methoxybenzaldehyde is distinct from that as the organic solvent.

In this case, at least a stoichiometric amount of dihalomethane relative to 4,5-dihydroxy-3-methoxybenzaldehyde is employed and a water-immiscible organic solvent is used. This organic solvent may be any organic solvent that is inert towards the reagents.

This may especially be an aromatic hydrocarbon such as, for example, benzene, toluene, chlorobenzenes and xylenes; an arylaliphatic ether such as, for example, anisole; an aliphatic or alicyclic hydrocarbon such as, for example, hexane or cyclohexane; an aliphatic ether such as, for example, dibutyl ether.

The ratio of aqueous phase:organic phase is such that phase separation occurs on standing.

The concentration of 4,5-dihydroxy-3-methoxybenzaldehyde in the aqueous phase is not critical. Most often, it depends on the previous stage for the preparation of the said 4,5-dihydroxy-3-methoxybenzaldehyde.

However, it is obvious that it is not economically advantageous to use too low a concentration as to provide an inadequate productivity of the equipment/apparatus.

The initial concentration of 4,5-dihydroxy-3-methoxybenzaldehyde in the aqueous phase typically ranges from 5% to 50% by weight.

The reaction is advantageously catalyzed by a conventional phase transfer catalyst. Compare, in this respect, the text *Phase Transfer Catalysis* by E. V. Dehmlov (Monograph in Modern Chemistry, Vol. 11, *Verlag Chemie*).

A quaternary ammonium compound (especially a halide) which is a conventionally known catalyst for this type of reaction is generally employed. This catalyst is preferably recycled.

Nor is the reaction temperature a critical feature of the process.

The reaction is generally carried out at a temperature of from 30° C. to 150° C. This temperature will preferably range from 50° C. to 120° C.

As mentioned above, the 4,5-dihydroxy-3-methoxybenzaldehyde may be prepared by hydrolyzing 5-halo-4-hydroxy-3-methoxybenzaldehyde. In this case, it is not necessary to isolate the 4,5-dihydroxy-3-methoxybenzaldehyde before reacting it, according to the process of the invention, with the dihalomethane.

The aqueous solution obtained in the preceding stage may be used directly.

In order to further illustrate the present invention and the advantages thereof, the following specific examples are given, it being understood that same are intended only as illustrative and in nowise limitative.

EXAMPLE 1

600 g (approximately 500 cm$^3$) of an aqueous solution having a pH of 9, containing the following materials in the form of sodium derivatives, were charged into a 1.5 liter stainless steel reactor equipped with an anchor stirrer, a heating system and a liquid injection system:

(i) 0.844 mole of 4,5-dihydroxy-3-methoxybenzaldehyde; and (ii) 0.200 mole of vanillin (impurity originating from the previous stages for the preparation of 4,5-dihydroxy-3-methoxybenzaldehyde).

670 g (approximately 500 cm$^3$) of dichloromethane and 80 g of tetrabutylammonium bromide were then added thereto.

The reactor was closed, swept with nitrogen and heated at 100° C., under stirring.

The pH of the reaction medium was maintained at a value of 9±0.5 by injecting therein an aqueous sodium hydroxide solution having a concentration of 30% by weight.

After 5 hr, 30 min, of reaction, the reaction mixture was cooled to ambient temperature and it was withdrawn. The mixture settled; the lower organic phase was separated and the aqueous phase was extracted with 2×250 cm$^3$ of dichloromethane.

The organic phase and the extracts obtained were combined.

The dichloromethane was distilled in order to recycle it into a subsequent operation.

The crude product obtained was washed with 250 cm$^3$ of water in order to extract the tetrabutylammonium bromide which will also be recycled into a subsequent experiment.

The crude product was then distilled under reduced pressure (approximately 65 pascals).

127.5 g of a fraction distilling at 110°–115° C. at the pressure mentioned above were obtained.

The NMR and the mass spectra were in agreement with the structure of 4,5-methylenedioxy-3-methoxybenzaldehyde.

The melting point of the product obtained was 134° C., which corresponds to the melting point of the reference product.

The yield of 4,5-methylenedioxy-3-methoxybenzaldehyde based on the 4,5-dihydroxy-3-methoxybenzaldehyde employed was 83%.

EXAMPLE 2

This example illustrates the combination of the reactions for the preparation of 4,5-dihydroxy-3-methoxybenzaldehyde starting with 5-bromo-4-hydroxy-3-methoxybenzaldehyde (bromovanillin) and the reaction of the 4,5-dihydroxy-3-methoxybenzaldehyde thus produced with dichloromethane.

The following materials were charged into the reaction employed in Example 1:

(i) 800 cm$^3$ of water;

(ii) 68.8 g of sodium hydroxide pellets;

(iii) 101 g of 5-bromo-4-hydroxy-3-methoxybenzaldehyde;

(iv) 1.6 g of copper powder.

The mixture was heated for 4 hours at 135° C., under stirring, in order to effect hydrolysis and produce 4,5-dihydroxy-3-methoxybenzaldehyde.

The mixture was then cooled to 100° C. and the pH was adjusted to a value of 8 by adding 50 cm$^3$ of 50% sulfuric acid.

The following materials were then charged:

265 g (approximately 200 cm$^3$) of dichloromethane;

14 g of tetrabutylammonium bromide.

The temperature was maintained at 100° C.

The pH was maintained at 8±0.1 by injecting an aqueous 30% by weight sodium hydroxide solution.

On completion of the reaction and after the treatments described in Example 1, an aqueous phase and an organic phase were separated.

The two phases were analyzed by high pressure liquid chromatography (HPLC).

The following results were obtained: rate of conversion of 5-bromo-4-hydroxy-3-methoxybenzaldehyde: 100%;

yield of 4,5-methylenedioxy-3-methoxybenzaldehyde: 41%;

yield of vanillin (determined in the aqueous phase): 9%; and yield of 4,5-dihydroxy-3-methoxybenzaldehyde (determined in the aqueous phase): 34%.

No product of reaction between the OH groups of the two compounds and the dichloromethane was observed.

EXAMPLE 3

The following materials were charged into a three necked round-bottomed flask made of glass, equipped with a magnetic stirrer, a condenser, an electrode for determining the pH of the reaction medium, a liquid introduction system and a thermometer:

(i) 250 g (100 cm$^3$) of dibromomethane;

(ii) 3.2 g of tetrabutylammonium bromide;

(iii) 17.7 g of 4,5-dihydroxy-3-methoxybenzaldehyde dissolved in 250 g of water.

The aqueous solution of 4,5-dihydroxy-3-methoxybenzaldehyde originated from a known synthesis, carried out in sequence, in several stages:

conversion of 2-methoxyphenol into 2,4-di(hydroxymethyl)-5-methoxyphenol;

oxidation of 2,4-di(hydroxymethyl)-5-methoxyphenol into 2,4-diformyl-5-methoxyphenol; and Dakin reaction on the aldehyde group located in the ortho position relative to OH in order to form the 4,5-dihydroxy-3-methoxybenzaldehyde.

The mixture was heated, under stirring, for 2 hr, 30 min, at 80° C., while maintaining the pH at approximately 9 by adding an aqueous sodium hydroxide solution.

After cooling and the usual treatment, the following results were obtained after analysis of the organic phase by HPLC:

rate of conversion of 4,5-dihydroxy-3-methoxybenzaldehyde: 100%; and yield of 4,5-methylenedioxy-3-methoxybenzaldehyde: 100%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of 3-methoxy-4,5methylenedioxybenzaldehyde, which comprises reacting 4,5-dihydroxy-3-methoxybenzaldehyde with dihalomethane in a two phase reaction medium comprising water and a liquid organic compound, at a pH ranging from 8 to 10.

2. The process as defined by claim 1, carried out in the presence of a catalytically effective amount of a phase transfer catalyst.

3. The process as defined by claim 1, wherein the dihalomethane comprises dichloromethane, dibromomethane, bromochloromethane, or mixture thereof.

4. The process as defined by claim 1, wherein the dihalomethane comprises both the reagent and the organic phase.

5. The process as defined by claim 1, wherein the organic phase comprises an inert solvent which is immiscible in water.

6. The process as defined by claim 5, wherein the organic solvent comprises an aromatic hydrocarbon, an arylaliphatic ether, an aliphatic or alicyclic hydrocarbon, or an aliphatic ether.

7. The process as defined by claim 2, wherein the phase transfer catalyst comprises a quaternary ammonium compound.

8. The process as defined by claim 1, wherein the pH is maintained at the desired value by adding an aqueous alkaline solution to the reaction medium.

9. The process as defined by claim 1, carried out at a temperature of from 30° C. to 150° C.

10. The process as defined by claim 1, wherein the initial concentration of 4,5-dihydroxy-3-methoxybenzaldehyde in the aqueous phase ranges from 5 to 50% by weight.

* * * * *